United States Patent
Bomkamp et al.

(10) Patent No.: US 9,000,204 B2
(45) Date of Patent: Apr. 7, 2015

(54) PROCESS FOR THE PREPARATION OF FLUOROALKYL (FLUORO)ALKYL CARBONATES AND CARBAMATES

(75) Inventors: Martin Bomkamp, Hannover (DE); Jens Olschimke, Hannover (DE)

(73) Assignee: Solvay Flour GmbH, Hannover (DE)

( * ) Notice: Subject to any disclaimer, the term of this patent is extended or adjusted under 35 U.S.C. 154(b) by 154 days.

(21) Appl. No.: 13/383,543

(22) PCT Filed: Jul. 8, 2010

(86) PCT No.: PCT/EP2010/059795
§ 371 (c)(1),
(2), (4) Date: Jan. 30, 2012

(87) PCT Pub. No.: WO2011/006822
PCT Pub. Date: Jan. 20, 2011

(65) Prior Publication Data
US 2012/0116111 A1    May 10, 2012

(30) Foreign Application Priority Data
Jul. 16, 2009    (EP) ..................... 09165665

(51) Int. Cl.
C07C 68/02    (2006.01)
C07C 269/04    (2006.01)
C07C 69/96    (2006.01)

(52) U.S. Cl.
CPC ............... *C07C 269/04* (2013.01); *C07C 68/02* (2013.01); *C07C 69/96* (2013.01)

(58) Field of Classification Search
None
See application file for complete search history.

(56) References Cited

U.S. PATENT DOCUMENTS

| 5,750,730 | A | 5/1998 | Nakano et al. |
| 6,010,806 | A | 1/2000 | Yokoyama et al. |
| 6,159,640 | A | 12/2000 | Appel et al. |
| 2004/0097758 | A1 | 5/2004 | Braun et al. |

FOREIGN PATENT DOCUMENTS

| CN | 101066965 | A | 11/2007 |
| DE | 1768660 | A1 | 1/1972 |
| DE | 19700656 | A1 | 7/1997 |
| EP | 0492386 | A1 | 7/1992 |
| GB | 909364 | A | 10/1962 |
| GB | 1216639 | A | 12/1970 |
| JP | 62290071 | A | 12/1987 |
| JP | 6009610 | A | 1/1994 |
| JP | 6329663 | A | 11/1994 |
| JP | 2004010491 | A | 1/2004 |
| JP | 2004161638 | A | 6/2004 |
| JP | 2006001843 | A | 1/2006 |
| WO | WO 2009118368 | A1 | 10/2009 |
| WO | WO 2009118369 | A1 | 10/2009 |
| WO | WO 2010136506 | A1 | 12/2010 |

OTHER PUBLICATIONS

Schlosser, Manfred, et al—"O-Fluoromethyl Carboxylates and O-Fluoromethyl Carbamates", 1995, Tetrahedron, vol. 51, Issue No. 20, pp. 5807-5812; 6 pgs.
Peng, Yong, et al—"Synthesis of 4-chloro-4,5-dimethyl-1,3-dioxolan-2-one", 2002, Jingxi Huagong Zhongjianti, vol. 32, Issue No. 2, pp. 20-21; 3 pgs, (includes abstract in English).
Kobayashi, Masafumi, et al—"Development of direct fluorination technology for application to materials for lithium battery", 2003, Journal of Fluorine Chemistry, vol. 120, Issue No. 2, pp. 105-110; 6 pgs.
Takehara, Masahiro, et al—"Synthesis of Fluorinated Dimethyl Carbamates by Direct Fluorination", 2004, Synthetic Communications, vol. 34, Issue No. 8, pp. 1367-1375; 9 pgs.
Hasegawa, Masaru, et al—"Regioselective Anodic Monofluorination of Ethers, Lactones, Carbonates and Esters Using Ionic Liquid Fluoride Salts", 2006, J. Electrochem. Soc., vol. 153, Issue 10, pp. D162-D166; 5 pgs.
Galimberti, Marco, et al—"New catalytic alkylation of in situ generated perfluoro-alkyloxy-anions and perfluoro-carbanions", 2005, Journal of Fluorine Chemistry, vol. 126, Issue No. 11-12, pp. 1578-1586; 9 pgs.
Senet, J. P., et al—"A Convenient New Route to I-Haloalkyl Carbonates", 1988, Synthesis, vol. 5, pp. 407-410; 5 pgs.
Wing Nja Sit, et al—"Coupling Reactions of CO2 with Neat Epoxides Catalyzed by PPN Salts to Yield Cyclic Carbonates" 2005, J. Org. Chem., vol. 70, Issue No. 21, pp. 8583-8586; 4 pgs.
Man Lok Man, et al—"Synthesis of Heterobimetallic Ru-Mn Complexes and the Coupling Reactions of Epoxides with Carbon Dioxide Catalyzed by these Complexes", 2006, Chemistry—A European Journal, vol. 12, Issue No. 4, pp. 1004-1015; 12 pgs.
Flosser, David A., et al —"A useful conversion of alcohols to alkyl fluorides", 2002, Tetrahedron Letters, vol. 43, Issue No. 23, pp. 4275-4279; 5 pgs.
Kawakami, Yuhsuke, et al—"Selectively Deuterated and Optically Active Cyclic Ethers", 1982, J. Org. Chem., vol. 47, Issue No. 18, pp. 3581-3585; 5 pgs.
Ishii, Hideki, et al—"Electrolytic partial fluorination of organic compound. Part:: 53* Highly regioselective anodic mono- and difluorination of 4-arylthio-1,3-dioxolan-2 ones. A marked solvent effect on fluorinated product selectivity", 2001,Tetrahedron, vol. 57, Issue No. 44, pp. 9067-9072; 6 pgs.
Dale, James A., et al—"Nuclear Magnetic Resonance Enantiomer Reagents. Configurational Correlations via Nuclear Magnetic Resonance Chemical Shifts of Diasteromeric Mandelate, O-Methylmandelate, and a-Methoxy-a-trifluoromethylphenylacetate (MTPA) Esters", 1973, J. Am. Chem. Soc., vol. 95, Issue No. 2, pp. 512-519, 8 pgs.

(Continued)

*Primary Examiner* — Alicia Otton

(57) ABSTRACT

Fluoroalkyl alkyl carbonates and fluorosubstituted carbamates which are suitable as additives or solvents in lithium ion batteries are prepared from fluoroalkyl fluoroformates and the respective alcohol or amine. Methanol is the preferred alcohol, dimethylamine and diethylamine are preferred amines. Fluoromethyl methyl carbonate is the preferred compound to be produced. Fluoroalkyl fluoroformates can be prepared from aldehydes and carbonyl fluoride.

11 Claims, No Drawings

(56) References Cited

OTHER PUBLICATIONS

Barcelo, Gerard, et al—"Alkyl 1-Chloroalkyl Carbonates, Reagents for the Synthesis of Carbamates and Protection of Amino Groups", 1986, Synthesis, vol. 8, pp. 627-632, XP-000891945; 6 pgs.

Dang, Vu Anh, et al—"A Simple Conversion of 1-Chloroethyl Carbonates to Fluoroformates: Value in the Preparation of Tertiary Alkyl Fluoroformates" and "Advantages of Fluoroformates as Carboalkoxylating Reagents for Polar Reactants", 1990, J. Org. Chem., vol. 55, Issue No. 6, pp. 1847-1851; 5 pgs.

Lange, Horst G., et al—"On the reactions of dimethylsulfoxide with acyl fluorides—pummerer rearrangements and formation of monofluoromethyl esters", 1985, Journal of Fluorine Chemistry, vol. 28, Issue No. 2, pp. 219-227; 9 pgs.

Theil, Fritz, et al—"Double Enantioselective Transesterification of Racemic Carboxylic Esters and Cyclic meso-Diols by Lipase Catalysis", 1994, J. Chem. Soc., Perkin Transactions 1, pp. 1509-1516; 8 pgs.

Nanbu, Noritoshi, et al—"Polar Effect of Successive Fluorination of Dimethyl Carbonate on Physical Properties", 2007, Bulletin of the Chemical Society of Japan, vol. 80, Issue No. 7 pp. 1302-1306; 5 pgs.

U.S. Appl. No. 12/933,503, filed Sep. 20, 2010, Harald Krueger, et al.

U.S. Appl. No. 13/321,270, filed Nov. 18, 2011, Martin Bomkamp, et al.

PROCESS FOR THE PREPARATION OF FLUOROALKYL (FLUORO)ALKYL CARBONATES AND CARBAMATES

CROSS-REFERENCE TO RELATED APPLICATIONS

This application is a U.S. national stage entry under 35 U.S.C. §371 of International Application No. PCT/EP2010/059795 filed Jul. 8, 2010, which claims priority benefit to European patent application number 09165665.2 filed on Jul. 16, 2009, the whole content of this application being incorporated herein by reference for all purposes.

The present invention concerns a process for the preparation of fluoroalkyl (fluoro)alkyl carbonates (i.e. fluoroalkyl alkyl carbonates and fluoroalkyl fluoroalkyl carbonates—the term in brackets denotes an optional fluorine substitution), especially of fluoromethyl methyl carbonate, and fluoroalkyl carbamates.

Fluoromethyl methyl carbonate is a known solvent additive for lithium ion batteries. It can be prepared by the reaction of dimethyl carbonate and elemental fluorine, as described in JP patent application 2004010491, or by electrochemical fluorination, see JP2006001843. Difluorinated products—difluoromethyl methyl carbonate and bis-fluoromethyl carbonate—and higher fluorinated products reduce yield and make separation processes necessary.

Partially fluorinated carbamates, as is described in U.S. Pat. No. 6,159,640 have a high thermal stability, a high flash point, a low vapor pressure, a high boiling point and other advantageous properties which make them suitable as solvents for lithium ion batteries, or as solvent additives for lithium ion batteries.

Object of the present invention is to provide a process which allows the selective manufacture of mono fluorinated fluoroalkyl alkyl carbonates and monofluoroalkyl fluoroalkyl carbonates, namely fluoroalkyl alkyl carbonates and especially fluoromethyl methyl carbonate, and of partially fluorinated carbamates.

The process according to the present invention provides for the manufacture of fluoroalkyl (fluoro)alkyl carbonates of the general formula (I), FCHR—OC(O)—OR', and for the manufacture of carbamates of general formula (VI), $R^1R^2N$—C(O)OCHRF, wherein the process for the manufacture of fluoroalkyl (fluoro)alkyl carbonates of the general formula (I), FCHR—OC(O)—OR' wherein R denotes linear or branched alkyl with 1 to 5 C atoms, $CH(CH_3)$=CH, $C(CH_3)_2$=CH, $CH_2$=CHX wherein X is $CH_2$, $C_2H_4$, or H and R' denotes linear or branched alkyl with 1 to 7 carbon atoms; linear or branched alkyl with 2 to 7 carbon atoms, substituted by at least one fluorine atom; phenyl; phenyl, substituted by 1 or more C1 to C3 alkyl groups atoms or phenyl substituted by 1 or more chlorine or fluorine atoms; or benzyl comprises a step of reacting a fluoroalkyl fluoroformate of formula (II), FCHROC(O)F, or a fluoroalkyl chloroformate of formula (II'), FCHROC(O)Cl, with an alcohol of formula (III), R'OH, wherein R and R' have the meanings given above, or comprises a step of reacting a chloroalkyl fluoroformate of formula (IV), ClCHROC(O)F, or a chloroalkyl chloroformate of formula (IV'), ClCHROC(O)Cl, wherein R has the meaning given above, with an alcohol of formula (III), R'OH wherein R' has the meaning given above, and a subsequent chlorine-fluorine exchange, or wherein the process for the manufacture of carbamates of general formula (VI), $R^1R^2N$—C(O)OCHRF, wherein $R^1$ and $R^2$ independently of one another are identical or different, linear C1 to C3 alkyl, branched C3 alkyl, wherein, optionally, one or more hydrogen atoms in the $R^1$ and $R^2$ groups are substituted by fluorine atoms, and wherein R denotes linear or branched alkyl with 1 to 5 C atoms, $CH(CH_3)$=CH, $C(CH_3)_2$=CH, or $CH_2$=CHX wherein X is a $CH_2$ or $C_2H_4$ group, comprises a step of reacting a fluoroalkyl fluoroformate of formula (II), FCHROC(O)F, or a fluoroalkyl chloroformate of formula (II'), FCHROC(O)Cl, with an amine of formula (VII), $R^1R^2NH$, wherein $R^1$ and $R^2$ have the meanings given above, or comprises a step of reacting a chloroalkyl fluoroformate of formula (IV), ClCHROC(O)F, or a chloroalkyl chloroformate of formula (IV'), ClCHROC(O)Cl, wherein R has the meaning given above, with an amine of formula (VII), $R^1R^2NH$, wherein $R^1$ and $R^2$ have the meanings given above, and a subsequent chlorine-fluorine exchange, Instead of the amine of formula (VII), a silylsubstituted amine can be applied, especially an amine of formula (IX), $R^1R^2NSiAlk_3$ wherein the Alk groups are the same or different and denote alkyl selected from the group consisting of methyl, ethyl and propyl. The reaction of the fluoroformiate and the amine can be performed in the presence of acid scavengers, e.g. in the presence of tertiary amines like trimethylamine or triethylamine.

Preferably, the process according to the present invention provides for the manufacture of fluoroalkyl (fluoro)alkyl carbonates of the general formula (I), FCHR—OC(O)—OR' wherein R denotes linear or branched alkyl with 1 to 5 C atoms or H and R' denotes linear or branched alkyl with 1 to 7 carbon atoms; linear or branched alkyl with 2 to 7 carbon atoms, substituted by at least one fluorine atom; phenyl; phenyl, substituted by 1 or more C1 to C3 alkyl groups atoms or phenyl substituted by 1 or more chlorine or fluorine atoms; or benzyl comprising a step of reacting a fluoroalkyl fluoroformate of formula (II), FCHROC(O)F, or a fluoroalkyl chloroformate of formula (II'), FCHROC(O)Cl, with an alcohol of formula (III), R'OH, wherein R and R' have the meanings given above, or comprising a step of reacting a chloroalkyl fluoroformate of formula (IV), ClCHROC(O)F, or a chloroalkyl chloroformate of formula (IV'), ClCHROC(O)Cl, wherein R has the meaning given above, with an alcohol of formula (III), R'OH wherein R' has the meaning given above, and a subsequent chlorine-fluorine exchange.

An especially preferred embodiment of the present invention provides for the manufacture of fluoroalkyl (fluoro)alkyl carbonates of the general formula (I), FCHR—OC(O)—OR', and for the manufacture of carbamates of general formula (VI), $R^1R^2N$—C(O)OCHRF, wherein the process for the manufacture of fluoroalkyl (fluoro)alkyl carbonates of the general formula (I), FCHR—OC(O)—OR' wherein R denotes linear or branched alkyl with 1 to 5 C atoms, $CH(CH_3)$=CH, $C(CH_3)_2$=CH, $CH_2$=CHX wherein X is $CH_2$, $C_2H_4$, or H and R' denotes linear or branched alkyl with 1 to 7 carbon atoms; linear or branched alkyl with 2 to 7 carbon atoms, substituted by at least one fluorine atom; phenyl; phenyl, substituted by 1 or more C1 to C3 alkyl groups atoms or phenyl substituted by 1 or more chlorine or fluorine atoms; or benzyl comprises a step of reacting a fluoroalkyl fluoroformate of formula (II), FCHROC(O)F, or a fluoroalkyl chloroformate of formula (II'), FCHROC(O)Cl, with an alcohol of formula (III), R'OH, wherein R and R' have the meanings given above.

The term "(fluoro)alkyl" indicates alkyl groups, including groups of the structure $CH(CH_3)=CH$, $C(CH_3)_2=CH$, $CH_2=CHX$ wherein X is a single bond, $CH_2$, or $C_2H_4$, and alkyl groups substituted by at least one fluorine atom. Consequently, the present invention provides for the manufacture of monofluorosubstituted fluoroalkyl alkyl carbonates and fluoroalkyl fluoroalkyl carbonates wherein one fluoroalkyl group is monosubstituted and the other fluoroalkyl group may be substituted by one or more fluorine atoms. In fluoroalkyl fluoroalkyl carbonates, the fluoroalkyl groups may be the same or different; at least one of the fluoroalkyl groups is monofluorinated.

Instead of the alcohol or additionally to the alcohol, a respective alkali metal alcoholate can be applied, for example, the respective lithium, sodium, potassium or cesium alcoholate. It is preferred to manufacture carbonates wherein R denotes C1 to C3 alkyl, $CH^2=CH-CH^2$, $CH(CH_3)=CH$, $C(CH_3)_2=CH$, or H, and more preferably, C1 to C3 alkyl or H. It is most preferred to manufacture carbonates wherein R is H. According to this preferred embodiment, a process is provided for the manufacture of fluoromethyl (fluoro)alkyl carbonates said process comprising a step of reacting fluoromethyl fluoroformate or fluoromethyl chloroformate and an alcohol, or, in an alternative, to react chloromethoxy chloroformate with an alcohol and to perform a subsequent chlorine fluorine exchange. It is especially preferred to use fluoromethyl fluoroformate which has the formula $FCH_2-O-C(O)F$.

The invention will now be explained in detail in view of the preferred alternative, namely the preparation of fluoroalkyl (fluoro)alkylcarbonates from fluoromethyl fluoroformate and an alcohol; also in this embodiment, the alcohol can be partially or completely be substituted by the respective alkali metal alcoholate, for example, by lithium, sodium, potassium or cesium alcoholate.

The alcohol preferably denotes a C1 to C5 alcohol; a C2 to C5 alcohol substituted by at least one fluorine atom; allyl alcohol; crotyl alcohol; prenyl alcohol; phenol or phenol, substituted by 1 or more C1 to C3 alkyl groups; or benzyl. Preferably, R' is a linear or branched C1 to C5 alkyl group, and thus, the alcohol is a C1 to C5 alkanol, more preferably, it is methanol, ethanol, n-propanol, i-propanol, allyl alcohol, n-butanol, i-butanol, 2-methylpropanol, n-pentanol, i-pentanol, or 2,2,2-trifluoroethanol. If trifluoroethanol is applied, it is possible to produce carbonates which comprise fluorine substituents on both alkoxy groups, for example, fluormethoxy-(2,2,2-trifluoroethoxy)carbonate or (1-fluoroethyl)-(2,2,2-trifluoroethoxy)carbonate. Especially preferably, the alcohol is methanol, ethanol, allyl alcohol, n-propanol and i-propanol. The most preferred alcohol is methanol.

If desired, a mixture of alcohols can be applied in a desired molar ratio. For example, a mixture of methanol and ethanol can be applied in a molar ratio of 1:1. In this case, a mixture of the respective methyl carbonate and ethyl carbonate in a molar ratio of approximately 1:1 is obtained.

The alcoholysis reaction can be performed in the presence of an HF scavenger e.g. LiF, NaF, KF or CsF, or in the presence of base, e.g. in the presence of ammonia or a primary, secondary or tertiary amine, e.g. triethylamine or pyridine. Preferably, it is performed in the absence of a base.

The molar ratio between alcohol and formate preferably is equal to or greater than 0.9:1. Preferably, it is equal to or lower than 5:1. Very good results are achieved when the ratio of alcohol and formate is in the range of 0.95:1 to 1.2:1.

The reaction temperature during the alcoholysis reaction is not critical. Often, the reaction is exothermic, thus, it may be advisable even to cool the reaction mixture, especially if an alkali metal alcoholate is applied. The temperature during alcoholysis is preferably equal to or higher than −80° C., more preferably, equal to or higher than −78° C. The upper temperature can be dependent from pressure and boiling point of the starting materials, e.g. from the boiling point of the alcohol. Often, the temperature is equal to or lower than 85° C.

The reaction can be performed in any suitable reactor, e.g. in an autoclave.

The reaction can be performed batch wise or continuously.

The resulting reaction mixture can be separated by known methods, e.g. by distillation, precipitation and/or crystallization. If desired, the reaction mixture can be contacted with water to remove water-soluble constituents. Due to the specific type of reaction, organic carbonates with a higher degree of fluorination are formed, if at all, in only very minor proportions.

According to another alternative, fluoroalkyl (fluor)alkyl carbonates of the general formula (I), $FCHR-OC(O)-OR'$ wherein R and R' have the meaning given above are prepared in a process comprising a step of reacting a chloroalkyl fluoroformate of formula (IV), $ClCHROC(O)F$, or a chloroalkyl chloroformate of formula (IV'), $ClCHROC(O)Cl$, wherein R has the meaning given above, with an alcohol of formula (III), R'OH wherein R' has the meaning given above, and a subsequent chlorine-fluorine exchange.

Thus, in a first step, an intermediate carbonate of formula (V), $ClCHR-OC(O)-OR'$, is produced. In this formula (V), R and R' have the meanings given above. This intermediate carbonate is then reacted with a reactant capable of substituting a fluorine atom for the chlorine atom. This reaction is known as "Halex" reaction. Reactants suitable to perform a chlorine-fluorine exchange are generally known. Especially suitable as such a reactant are alkaline or alkaline earth metal fluorides, ammonium fluoride, amine hydrofluorides of formula (IX), $N(R^1)_4F$ wherein the substituents $R^1$ are the same or different and denote H or C1 to C5 groups with the proviso that at least 1 substituent $R^1$ is a C1 to C5 alkyl group. Also amine hydrofluorides are suitable in which the nitrogen atom is part of a heterocyclic ring system, for example, pyridinium hydrofluoride, 1,8-diazabicyclo[5.4.0]undec-7-ene, and 1,5-diaza-bicyclo[4.3.0]non-5-ene. Instead of the fluorides, or additionally to them, hydrofluoride adducts can be used for the Halex reaction, e.g. CsF.HF. Other fluorides are likewise suitable as reactant, e.g. AgF. The Halex reaction can be performed in the absence or in the presence of a solvent, for example, in the presence of a nitrile. Often, the reaction is performed at elevated temperature, e.g. at a temperature equal to or higher than 50° C.

The workup of the reaction mixture which comprises the chloride salt and possibly excess fluoride salt of the fluorinating reactant, and the fluorinated carbonate and possibly unreacted starting material, is performed in a known manner. For example, solids are removed by filtration, and the liquid phase is subjected to a fractionated distillation or precipitation after removal of any solvents.

The fluorinated organic carbonates produced by the process of the present invention are useful as additives or solvents for lithium ion batteries. They provide advantages like modifying the viscosity, reduce flammability and appear to modify the electrodes under formation of beneficial films.

Preferred amines $R^1R^2NH$ for the manufacture of carbamates are those wherein R1 and R2 are the same or different and correspond to methyl, ethyl, n-propyl and i-propyl. As to the manufacture of the carbamates, the molar ratio between amine and formate is preferably equal to or greater than 0.9:1. If the amine functions also as acid scavenger, the ratio is preferably equal to or greater than 1.8:1. Preferably, the ratio between amine and formate is equal to or lower than 5:1. Preferably, the ratio between amine and formate are between 0.95:1 to 1.2:1, or, if the amine functions as a base, in the range of 1.9:1 to 2.4:1. The reaction temperature is preferably in the range of 0 to 50° C. The workup of the reaction mixtures is performed in a known manner. Solids are filtered off, and the carbamates can be isolated from the resulting liquid raw product by distillation.

Compounds of formula (II), FCHROC(O)F, can be prepared from the respective chloroalkyl chloroformates in a "Halex" type reaction, i.e. substitution of fluorine atoms for the chlorine atoms by fluorinating agents, as already described above, e.g. using a fluorinating reactant like alkali or alkaline earth metal fluorides, e.g. LiF, KF, CsF, NaF, $NH_4F$ or amine hydrofluorides, or the respective HF adducts. The chloroalkyl chloroformates themselves are available through the reaction between phosgene and an aldehyde as described in U.S. Pat. No. 5,712,407. It is preferred to produce the intermediate compounds of formula (II), FCHROC(O)F, from carbonyl fluoride and an aldehyde. Thus, another aspect of the present invention concerns a process for the manufacture of intermediate compounds of formula (II), FCHROC(O)F, from carbonyl fluoride and an aldehyde of formula RC(O)H wherein R denotes linear or branched alkyl with 1 to 5 C atoms or H. Preferably, it denotes H; here, the aldehyde is formaldehyde. The formaldehyde can be can be applied in the form of paraformaldehyde or trioxane which must be cracked, e.g. thermally, to form the monomeric formaldehyde.

The molar ratio between carbonyl fluoride and the aldehyde is preferably equal to or greater than 0.9:1. It is preferably equal to or lower than 5:1.

Preferably, the molar ratio between carbonyl fluoride and aldehyde is in the range of 0.9:1 to 5:1. More preferably, the molar ratio between carbonyl fluoride and aldehyde is in the range of 0.9:1 to 3:1.

Preferably, the reaction between carbonyl fluoride and the aldehyde is catalyzed.

The reaction can be catalyzed, for example, by $F^-$. For example, the reaction can be catalyzed by HF, which may be added as such or prepared in situ by the addition of low amounts of water.

Preferred catalysts are those which contain fluoride anions, e.g. alkaline earth metal fluorides or alkali metal fluorides such as CsF, or catalysts which contain fluoride ions formed from carbonyl fluoride and a pre-catalyst. Preferred pre-catalysts are dialkyl formamides, especially dimethyl formamide. It is assumed that the formamide and carbonyl fluoride form a "naked" fluoride ion which starts a nucleophilic reaction on the aldehyde. The negatively charged oxygen of the formed adduct of the fluoride ion and the aldehyde molecule then reacts with a carbonyl fluoride molecule forming fluoromethyl fluoroformate or generally, the fluoroalkyl fluoroformate.

Pyridine, advantageously 4-dialkylaminopyridines, especially 4-dimethylaminopyridine, are also considered as suitable pre-catalysts.

The reaction preferably is performed batch wise, e.g. in an autoclave. Alternatively, it can be performed continuously.

The reaction temperature can vary. For example, when a very effective catalyst is applied, the reaction may even be performed at ambient temperature. It has to be kept in mind, however, that in the case of formaldehyde as starting material, the monomeric form must be provided by cracking of paraformaldehyde or 1,3,5-trioxane. Thus, while the reaction as such often could be performed at low temperature, nevertheless heat must be applied for cracking.

In the case of formaldehyde as starting material, the reaction preferably is performed at a temperature equal to or higher than 100° C. It is preferably performed at a temperature equal to or lower than 300° C. When aldehydes are used as starting material which must not be thermally cracked, the reaction can be performed at a temperature equal to or higher than 0° C. and equal to or lower than 200° C. It is preferred to perform the reaction at such an elevated temperature and/or for a sufficient time until the desired conversion has taken place.

It is performed in the liquid phase or under supercritical conditions. The pressure is selected such that at least a part of the carbonyl fluoride is present in the liquid phase. The pressure depends from the reaction temperature; the higher the reaction temperature, the higher is the pressure in the reactor. The reaction can be performed at ambient pressure (about 1 Bar absolute). For example, $COF_2$ can be introduced into the liquid reaction mixture or starting material though an immersed pipe. Preferably, the reaction is performed at a pressure equal to or higher than 5 bar (abs.). Preferably, the reaction is performed at a pressure equal to or lower than 50 bar (abs.). If, as done in one example, the reaction temperature is sufficiently high, the content of the reactor is in a supercritical state. The reaction vessel can be pressurized, if desired, with an inert gas, especially with nitrogen.

If desired, the fluoroalkyl fluoroformates, and especially the fluoromethyl fluoroformate, can be isolated from the reaction mixture according to methods known in the art, e.g. by distillation. The fluorosubstituted formates formed can be applied for any purposes for which compounds with a C(O)F function or a $FCH_2O$ function are used. For example, they can be used as fluorinating agent or to introduce a protecting group in aminoacids or peptides. In a preferred embodiment, the formates are reacted, as described above, with an alcohol to produce fluoromethyl alkyl esters of carbonic acid.

A preferred aspect of the present invention concerns a process comprising 2 or 3 steps for the manufacture of compounds of formula (I), FCHROC(O)—OR', wherein R denotes linear or branched alkyl with 1 to 5 C atoms or H and R' denotes linear or branched alkyl with 1 to 7 carbon atoms; linear or branched alkyl with 2 to 7 carbon atoms substituted by at least one fluorine atom; phenyl; benzyl; phenyl, substituted by 1 or more C1 to C3 alkyl groups atoms or phenyl substituted by 1 or more chlorine or fluorine atoms. This process is performed according to two alternatives.

The first alternative comprises:

A step of preparing a fluoroalkyl fluoroformate of formula (II), FCHROC(O)F, from carbonyl fluoride and an aldehyde RC(O)H wherein R denotes linear or branched alkyl with 1 to 5 C atoms or H; and a step of reacting the fluoroalkyl fluoroformate of formula (II) with an alcohol of formula (III), R'OH, wherein R and R' have the meanings given above.

Instead of the alcohol or additionally to the alcohol, the respective alkali metal alcoholate can be applied, for example, the respective potassium or sodium alcoholate.

Also here, the group R preferably denotes H, and the aldehyde concerned is formaldehyde. The formaldehyde can be applied in the form of paraformaldehyde or 1,3,5-trioxane which must be cracked, e.g. thermally, to form the monomeric formaldehyde.

A preferred embodiment of this 2-step process according to the present invention provides for the manufacture of fluoromethyl alkyl carbonates comprising:

A step of preparing fluoromethyl fluoroformate from carbonyl fluoride and formaldehyde, 1,3,5-trioxane or paraformaldehyde, and, with or without isolation, and subsequently, A step of reacting the fluoromethyl fluoroformate with an alcohol of formula (III), R'OH, wherein R' preferably denotes linear or branched alkyl with 1 to 7 C atoms; $CH_2=CHX$ wherein X is $CH_2$ or $C_2H_4$; $CH(CH_3)=CH$, $C(CH_3)_2=CH$; phenyl; phenyl, substituted by 1 or more C1 to C3 alkyl groups atoms or phenyl substituted by 1 or more chlorine or fluorine. Preferably, the alcohol is selected from the group consisting of methanol, ethanol, n-propanol, i-propanol, allyl alcohol, n-butanol and n-pentanol. Especially preferably, the alcohol is allyl alcohol, methanol or ethanol, and most preferably, methanol.

Preferred embodiments of the steps are those already described above, especially what concerns the preferred use of a catalyst, using a formamide, especially dimethyl formamide, as preferred pre-catalyst in the first step, the pressure and temperature in the first and second step, the optional use of a base in the second step, the respective pressures, reaction temperatures etc; the preferred embodiments described above for the respective reaction steps apply also for the 2-step process of the invention.

The other alternative comprises a process which includes a Halex reaction.

In this alternative, in a first step, carbonyl chloride (phosgene) is reacted with RC(O)H wherein R denotes linear or branched alkyl with 1 to 5 C atoms or H. The formed intermediate chloroalkyl chloroformate of formula (IV'), ClCHR-C(O)Cl wherein R has the meaning given above is then either subjected to a Halex reaction to form the fluoroalkyl formate of formula (I) which is then reacted with an alcohol or an alcoholate as described above to produce the fluoroalkyl (fluoro)alkyl carbonates of formula (I); or the formed intermediate chloroalkyl chloroformate of formula (VII), ClCH-ROC(O)Cl wherein R has the meaning given above, is then reacted with an alcohol or an alcoholate as described above to produce the chloroalkyl (fluoro)alkyl carbonate of formula (V) which then is subjected to a Halex reaction as described above to produce the fluoroalkyl (fluoro)alkyl carbonates of formula (I).

Another preferred aspect of the present invention concerns a process for the manufacture of compounds of formula (VI), $R^1R^2N-C(O)-OCHFR$, wherein R denotes linear or branched alkyl with 1 to 5 C atoms and $R^1$ and $R^2$ have the meaning given above. This process is performed according to two alternatives.

The first alternative comprises:

A step of preparing a fluoroalkyl fluoroformate of formula (II), FCHROC(O)F, from carbonyl fluoride and an aldehyde RC(O)H wherein R denotes linear or branched alkyl with 1 to 5 C atoms or H; and a step of reacting the fluoroalkyl fluoroformate of formula (II) with an amine of formula (VIII), $R^1R^2NH$, wherein $R^1$ and $R^2$ have the meanings given above.

Another embodiment of the present invention are chloroalkyl fluoroalkyl carbonate intermediates of formula (V'), ClCHRC(O)OR'' wherein R denotes linear or branched alkyl with 1 to 5 C atoms or H and wherein R'' denotes linear or branched alkyl with 1 to 7 carbon atoms, substituted by at least one fluorine atom. Preferably, in compounds of formula (V'), R denotes CH3 or H, and R'' denotes 2,2,2-trifluoroethyl, with the exception of 1-chloroethyl 2,2,2-trifluoroethyl carbonate.

These intermediates can be prepared from 1-chloroalkyl chloroformates and a fluorinated alcohol or the alcoholate of a fluorinated alcohol, e.g. the lithium, sodium, potassium or cesium alcoholate of a fluorinated alcohol; trifluoroethanolates are possibly instable. These intermediates can be used, as described, as starting material to produce the fluoroalkyl fluoroalkyl carbonates of the present invention. They can also be used as intermediates in chemical synthesis.

The process of the present invention concerning the preparation of fluoromethyl alkyl carbonates allows for the selective production of monofluorinated products; higher fluorinated products are formed, if at all, in only minor amounts. The compounds can be used neat as a solvent in the Li ion batteries, or, as an additive, e.g. for reducing the viscosity of the solvent. The amount as an additive is, for example, in a range from 0.5 to 60% by weight.

Since a main application field for the compounds of formula (I) is the use as solvents or additives in lithium ion batteries, it is preferred not start from chlorinated compounds because chlorine is undesired as impurity in the technical field. Thus, the reaction path without the necessity of Halex reactions is preferred.

Compounds wherein R has the meaning of $CH(CH_3)=CH$, $C(CH_3)_2=CH$, $CH_2=CHX$ wherein X is $CH_2$, $C_2H_4$, preferably $CH_2$, are suitable as monomers for copolymerization reactions.

Should the disclosure of any patents, patent applications, and publications which are incorporated herein by reference conflict with the description of the present application to the extent that it may render a term unclear, the present description shall take precedence.

The invention will now be further described in examples without intending to limit it.

EXAMPLE 1

Preparation of Fluoromethyl Fluoroformate

Paraformaldehyde (10.2 g; 340 mmol) and dimethylformamide (1.5 g; 71 mmol) were given into an autoclave with an internal volume of about 500 ml. The autoclave was closed, evacuated and pressurized to about 5 bar (abs.) with dry nitrogen and evacuated again. Then, carbonyl fluoride (32 g; 485 mmol) was given into the autoclave. The autoclave was heated overnight to about 230° C.; the pressure rose to about 35 bar (abs.). Then, the autoclave was cooled to ambient temperature, the pressure fell now to about 10 bar (abs.). Gaseous components of the autoclave were purged through a washer. The autoclave was then pressurized two times with nitrogen, each time up to a pressure of about 5 bar (abs.).

If desired, fluoromethyl fluoroformate formed can be isolated by distillation.

EXAMPLE 2

Preparation of Fluoromethyl Methyl Carbonate ("FlDMC")

Into the autoclave cooled to −10° C. containing the reaction residue of example 1, methanol (10 ml; 247 mmol) is added. The autoclave was closed, and the reaction mixture was stirred overnight at ambient temperature. A sample was taken from the reaction mixture and analyzed by gas chromatography (GC) and gas chromatography/mass spectrum (GC-MS). The reaction mixture contained FlDMC in about 25% (area in GC). Further, methanol and dimethoxymethane were identified (the latter obtained probably as reaction product of excess methanol and formaldehyde).

If desired, the reaction mixture can be washed with water to remove water-soluble constituents. After drying, e.g. using $MgSO_4$, fluoromethyl methyl carbonate can be isolated in pure form by distillation.

EXAMPLE 3

Preparation of Fluoroethyl Fluoroformate

Acetaldehyde (12 g; 272 mmol) and dimethylformamide (200 mg; 71 mmol) were given into an autoclave with an internal volume of about 40 ml. The autoclave was closed, evacuated and pressurized to about 5 bar (abs.) with dry nitrogen and evacuated again. Then, carbonyl fluoride (18 g; 272 mmol) was given into the autoclave over a period of 30 min. The mixture was stirred at room temperature for 30 min after which the pressure fell from 20 bar to 0 bar. The autoclave was then pressurized two times with nitrogen, each time up to a pressure of about 5 bar (abs.).

If desired, fluoroethyl fluoroformate formed can be isolated by distillation.

EXAMPLE 4

Preparation of Fluoroethyl Methyl Carbonate ("FlEMC")

In a 100 mL PFA-flask fluoroethyl fluoroformate (24.7 g, 225 mmol) was cooled to −78° C. Methanol (12 mL, 310 mmol) was added over a period of 15 min. The mixture was stirred at −78° C. for 30 min. After warming up to room temperature the reaction was stirred for further 16 h. The resulting mixture was washed with water (3×10ml), molecular sieve (0.4 nm) was added, and after stirring for 4 h at room temperature, all solids were removed by filtration and the resulting crude product was purified by distillation under reduced pressure (100 mbar).

The boiling point was 50° C. at a pressure of 200 mbar.
Yield: 19.1 g (70% of theory).

EXAMPLE 5

Preparation of Fluoroethyl Ethyl Carbonate ("FlDEC")

In a 100 mL PFA-flask fluoroethyl fluoroformate (27.0 g, 245 mmol) was added to dry NaF (15 g; 357 mmol). After cooling the mixture to −78° C. ethanol (12 mL, 310 mmol) was added over a period of 15 min. The mixture was stirred at −78° C. for 30 min. After warming up to room temperature the reaction was stirred for further 16 h. After addition of 5 g molecular sieve (0.4 nm) and stirring for 4 h at room temperature, all solids were removed by filtration and the resulting crude product was purified by distillation under reduced pressure (100 mbar).

EXAMPLE 6

Preparation of Fluoromethyl Methyl Carbonate Including a Halex Reaction

In a 100 ml, one necked flask equipped with a dropping funnel, a solution of chloromethyl chloroformate (10.0 g; 78 mmol) in 30 mL diethyl ether was cooled to 0° C. Over a period of 15 minutes a mixture of methanol (4 mL, 100 mmol) and pyridine (7 mL, 86 mmol) was added slowly to the stirred solution and kept at 0° C. for 2 h. The obtained white precipitate was removed by filtration and the resulting solution was added to a mixture of potassium fluoride (9 g, 145 mmol) and 18-crown-6 (1.2 g, 5 mmol). After stirring the mixture for 18 h, formation of fluoromethyl methyl carbonate could be proven by GC and MS.

EXAMPLE 7

Preparation of $Et_2N$—C(O)$OCH_2F$

In a 100 mL PFA-flask, fluoromethyl formate (27.0 g, 245 mmol) is given. Diethylamine (50.5 mL; 0.490 mmol) is added dropwise at about 0° C. The mixture is stirred for 1 hour. Solids are filtered off, and the resulting liquid is subjected to a distillation to isolate pure fluoromethyl N,N-diethylcarbamate.

The invention claimed is:

1. A process for the manufacture of fluoroalkyl carbonates of the general formula (I), FCHR—OC(O)—OR',
    wherein R is selected from the group consisting of linear or branched alkyl with 1 to 5 carbon atoms; $CH_2$=CHX wherein X is $CH_2$ or $C_2H_4$; $CH(CH_3)$=CH; $C(CH_3)_2$=CH; and H, and wherein R' is selected from the group consisting of linear or branched alkyl with 1 to 7 carbon atoms; linear or branched alkyl with 2 to 7 carbon atoms, substituted by at least one fluorine atom; phenyl; phenyl substituted by one or more C1 to C3 alkyl groups; phenyl substituted by one or more chlorine or fluorine atoms; and benzyl;
    said process comprising a step of reacting a fluoroalkyl fluoroformate of formula (II), FCHROC(O)F, with an alcohol of formula (III), R'OH, wherein R and R' have the same meanings as for formula I.
2. The process of claim 1 wherein R is H.
3. The process of claim 1 wherein R' is a C1 to C5 alkyl.
4. The process of claim 3 wherein R' is selected from the group consisting of methyl, ethyl, n-propyl, and isopropyl.
5. The process of claim 1 wherein the molar ratio between the alcohol and said fluoroalkyl fluoroformate of formula (II) is 0.9:1 to 5:1.
6. The process of claim 1 wherein the fluoroalkyl fluoroformate of formula (II) is prepared from carbonyl fluoride and an aldehyde of formula RC(O)H wherein R is H or a linear or branched alkyl with 1 to 5 carbon atoms.
7. The process of claim 6 wherein the fluoroalkyl fluoroformate of formula (II) is fluoromethyl fluoroformate which is prepared from a reaction between carbonyl fluoride and formaldehyde.
8. The process of claim 6 wherein the reaction between carbonyl fluoride and formaldehyde is performed in the presence of fluoride ($F^-$).
9. The process of claim 8 wherein the fluoride is formed from carbonyl fluoride and a pre-catalyst.
10. The process of claim 9 wherein the pre-catalyst is dimethyl formamide.
11. The process of claim 6 wherein the molar ratio between carbonyl fluoride and aldehyde is in the range of 0.9:1 to 5:1.

* * * * *